(12) United States Patent
Freedman et al.

(10) Patent No.: US 8,961,895 B2
(45) Date of Patent: Feb. 24, 2015

(54) AIR TREATMENT SYSTEM

(71) Applicants: Barney Freedman, Jacksonville Beach, FL (US); Boyd Alin, Esquimalt (CA)

(72) Inventors: Barney Freedman, Jacksonville Beach, FL (US); Boyd Alin, Esquimalt (CA)

(73) Assignee: Akida Holdings, LLC, Jacksonville, FL (US)

( * ) Notice: Subject to any disclaimer, the term of this patent is extended or adjusted under 35 U.S.C. 154(b) by 25 days.

(21) Appl. No.: 13/756,810

(22) Filed: Feb. 1, 2013

(65) Prior Publication Data
US 2013/0202494 A1 Aug. 8, 2013

Related U.S. Application Data

(60) Provisional application No. 61/594,575, filed on Feb. 3, 2012.

(51) Int. Cl.
*A62B 7/08* (2006.01)
*A61L 9/00* (2006.01)
*A61N 5/00* (2006.01)
*A61L 9/20* (2006.01)

(52) U.S. Cl.
CPC .. *A61L 9/00* (2013.01); *A61L 9/205* (2013.01)
USPC ......... 422/306; 250/492.1; 204/252; 315/297

(58) Field of Classification Search
CPC ............. A61L 9/00; A61L 9/032; A61L 9/18; A61L 9/20; A61L 9/205
USPC ............... 422/5, 22, 24, 124, 306; 250/492.1; 204/252; 315/297
See application file for complete search history.

(56) References Cited

U.S. PATENT DOCUMENTS

| 2006/0219235 | A1* | 10/2006 | Bagwell et al. | 126/299 R |
| 2009/0280027 | A1* | 11/2009 | Hayman, Jr. | 422/4 |
| 2010/0047115 | A1 | 2/2010 | Krichtafovitch et al. | |

OTHER PUBLICATIONS

U.S. International Searching Authority, International Search Report and Written Opinion issued in corresponding International Application No. PCT/US2013/24319, dated Apr. 11, 2013.

* cited by examiner

*Primary Examiner* — Monzer R Chorbaji
(74) *Attorney, Agent, or Firm* — Holland & Knight LLP; Brian J. Colandreo, Esq.; Jeffrey T. Placker, Esq.

(57) ABSTRACT

An air treatment system may include a housing including at least one wall defining a nozzle passage having a vent adjacent an upstream portion of the at least one wall. The air treatment system may also include a photocatalytic reaction chamber including a plurality of photocatalytic media and a light source disposed to illuminate at least a portion of the photocatalytic media for producing a photocatalytic reaction generating a plurality of hydroxyl radicals. The air treatment system may also include a blower fluidly coupled with the photocatalytic reaction chamber for conveying air through the photocatalytic reaction chamber and directing the air through the vent and along at least a portion of the at least one wall.

21 Claims, 13 Drawing Sheets

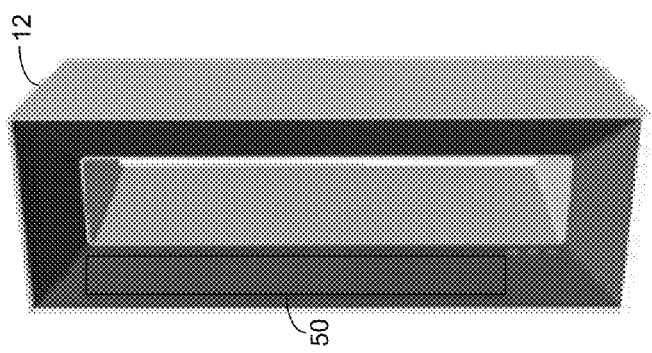
FIG. 12

AIR TREATMENT SYSTEM

CROSS-REFERENCE TO RELATED APPLICATIONS

This application claims the benefit of U.S. provisional patent application Ser. No. 61/594,575, entitled "Consumer Airocide Product," filed on 3 Feb. 2012, the entire disclosure of which is incorporated herein by reference.

TECHNICAL FIELD

The present disclosure generally relates to air treatment systems, and more particularly relates to photocatalytic air treatment systems.

BACKGROUND

Fans may often be used in a variety of settings, and for a variety of purposes. For example, fans may often be utilized to provide localized air movement or circulation to improve user comfort, etc. For example, table-top, window, and ceiling fans are often uses to induce movement in otherwise stagnant air. Creating such air movement may give rise to convective cooling, or the sensation of a breeze, which may allow a user of the fan to experience a cooling sensation or effect. Additionally, such fans may often be used to normalize temperatures in a room. For example, regions of a room that are proximate a heating or cooling source (such as a heating/air conditioning heat exchanger or vent) may experience a different temperature than other regions of the room that are farther away from the heating or cooling source. Air circulation provided by a fan may cause movement and mixing of the air between the different regions of the room, which may cause the overall temperature of the room to normalize, thereby providing a more comfortable or desirable effect.

SUMMARY

According to an implementation, an apparatus may include a housing including at least one wall defining a nozzle passage having a vent adjacent an upstream portion of the at least one wall. The apparatus may also include a photocatalytic reaction chamber including a plurality of photocatalytic media and a light source disposed to illuminate at least a portion of the photocatalytic media for producing a photocatalytic reaction generating a plurality of hydroxyl radicals. The apparatus may further include a blower fluidly coupled with the photocatalytic reaction chamber for conveying air through the photocatalytic reaction chamber and directing the air through the vent and along at least a portion of the at least one wall.

One or more of the following features may be included. The nozzle passage may include a Coanda surface adjacent to the vent. A first portion of the at least one wall may diverge outwardly relative to an axis of the nozzle passage downstream from the vent. A second portion of the at least one wall may diverge outwardly away from the first portion of the wall relative to the axis of the nozzle passage downstream from the first portion of the wall.

The housing may include at least two generally opposed walls defining the nozzle passage. Each wall may include a vent adjacent and upstream portion of each wall. The nozzle passage may have a generally quadrilateral cross-section.

The housing may define a housing interior at least partially surrounding the nozzle passage. The photocatalytic reaction chamber and the blower may be at least partially disposed within the housing interior. The housing may further define a passage fluidly coupling the blower, the photocatalytic reaction chamber, and the vent.

The photocatalytic reaction chamber may include a removable reaction chamber cartridge. The plurality of photocatalytic media and the light source may be at least partially contained within the reaction chamber cartridge. The photocatalytic media may include a media substrate coated with a micro-porous nano-particle membrane including a photocatalytic substance. The photocatalytic substance may include $TiO_2$ and the light source may emit ultraviolet light having a wavelength less than about 400 nm. The photocatalytic substance may include at least one of ZnO and a $WO_3$, and the light source may emit light in the visible spectrum.

The blower may be configured to push the air through the photocatalytic reaction chamber. The blower may be configured to pull the air through the photocatalytic reaction chamber.

According to another implementation, an apparatus may include a housing defining a nozzle passage having at least one Coanda exhaust adjacent to an upstream portion of the nozzle passage. The apparatus may also include a photocatalytic reaction chamber cartridge at least partially disposed within an interior defined by the housing and removably coupled with the housing. The photocatalytic reaction chamber cartridge may include a photocatalytic reaction chamber including a plurality of photocatalytic media and a light source disposed to illuminate at least a portion of photocatalytic media for producing a plurality of hydroxyl radicals from a photocatalytic reaction of the photocatalytic media. The apparatus may further include a blower at least partially disposed within the interior defined by the housing and fluidly coupled with the photocatalytic reaction chamber cartridge and the at least one Coanda exhaust for conveying air through the photocatalytic reaction chamber and out through the at least one Coanda exhaust.

One or more of the following features may be included. The photocatalytic media may include a substrate coated with a micro-porous nano-particle membrane of a photocatalytic substance. The photocatalytic media may include a $TiO_2$ photocatalytic substance, and the light source includes a UV light source emitting light having a wavelength less than about 400 nm. The photocatalytic media may include one of a ZnO and a $WO_3$ photocatalytic substance, and the light source emits light in the visible spectrum.

The housing may include four walls defining the nozzle passage having a generally rectangular cross-section. The apparatus may include at least two generally opposed Coanda exhausts associated with two generally opposed walls defining the nozzle passage. The apparatus may include two photocatalytic reaction chamber cartridges. One photocatalytic reaction chamber cartridge may be associated with each of the two generally opposed Coanda exhausts.

According to another implementation, an apparatus may include a housing including four walls defining a nozzle passage having a generally rectangular cross-section. Two opposed walls may include a respective Coanda exhaust adjacent to an upstream portion of the nozzle passage. The apparatus may also include a photocatalytic reaction chamber cartridge at least partially disposed within an interior defined by the housing and removably coupled with the housing. The photocatalytic reaction chamber cartridge may include a photocatalytic reaction chamber including a plurality of photocatalytic media and a light source disposed to illuminate at least a portion of photocatalytic media for producing a plurality of hydroxyl radicals from a photocatalytic reaction of the photocatalytic media. The apparatus may also include a blower at least partially disposed within the interior defined by the housing and fluidly coupled with the photocatalytic reaction chamber cartridge and the at least one Coanda exhaust for conveying air through the photocatalytic reaction chamber and out through the at least one Coanda exhaust.

The details of one or more implementations are set forth in the accompanying drawings and the description below. Other features and advantages will become apparent from the description, the drawings, and the claims.

BRIEF DESCRIPTION OF THE DRAWINGS

FIG. 12 is an diagrammatically depicts an air treatment apparatus including a removable grill portion, according to an example embodiment of the present disclosure.

DETAILED DESCRIPTION OF ILLUSTRATIVE EMBODIMENTS

According to various embodiments, an air treatment apparatus may be provided that may be capable of being provided as a relatively compact system. The air treatment apparatus may provide a relatively high efficiency of air treatment through the killing and/or mineralizing bacteria, mold, fungi, spores, mycotoxins, viruses, allergens, other similar organic microorganisms or agents, and/or oxidizing volatile organic compounds (VOC's). As such, an air treatment apparatus consistent with some embodiments of the present disclosure may facilitate an improvement of air quality in a space (e.g., such as a room or portion of a room) in which the air treatment apparatus is used.

In some embodiments, some embodiments the air treatment apparatus may eliminate the use of an exposed fan configuration. For example, the air treatment apparatus may generally utilize a nozzle or duct configuration in which an airflow through the nozzle or duct may be induced, e.g., by creating a relative low pressure zone in at least a downstream region of the air treatment apparatus. The induced airflow through the nozzle may, in some embodiments, increase overall airflow of the air treatment apparatus. Increasing the overall airflow through the nozzle of the air treatment apparatus may, for example, increase the distribution of treated air throughout the space (e.g., room, or other space) in which the air treatment apparatus is utilized. Further, the increased overall airflow provided by the air treatment apparatus may combine benefits of air treatment with air circulating effects. In some such embodiments, not only may the air treatment apparatus clean the air, but the air treatment apparatus may also provide climate regulating or modifying benefits.

In an embodiment, an air treatment apparatus may generally include a housing including at least one wall defining a nozzle passage having a vent adjacent an upstream portion of the at least one wall. The air treatment apparatus may also include a photocatalytic reaction chamber including a plurality of photocatalytic media and a light source disposed to illuminate at least a portion of the photocatalytic media for producing a photocatalytic reaction generating a plurality of hydroxyl radicals. The apparatus may further include a blower fluidly coupled with the photocatalytic reaction chamber for conveying air through the photocatalytic reaction chamber and directing the air through the vent and along at least a portion of the at least one wall.

Figure 1:
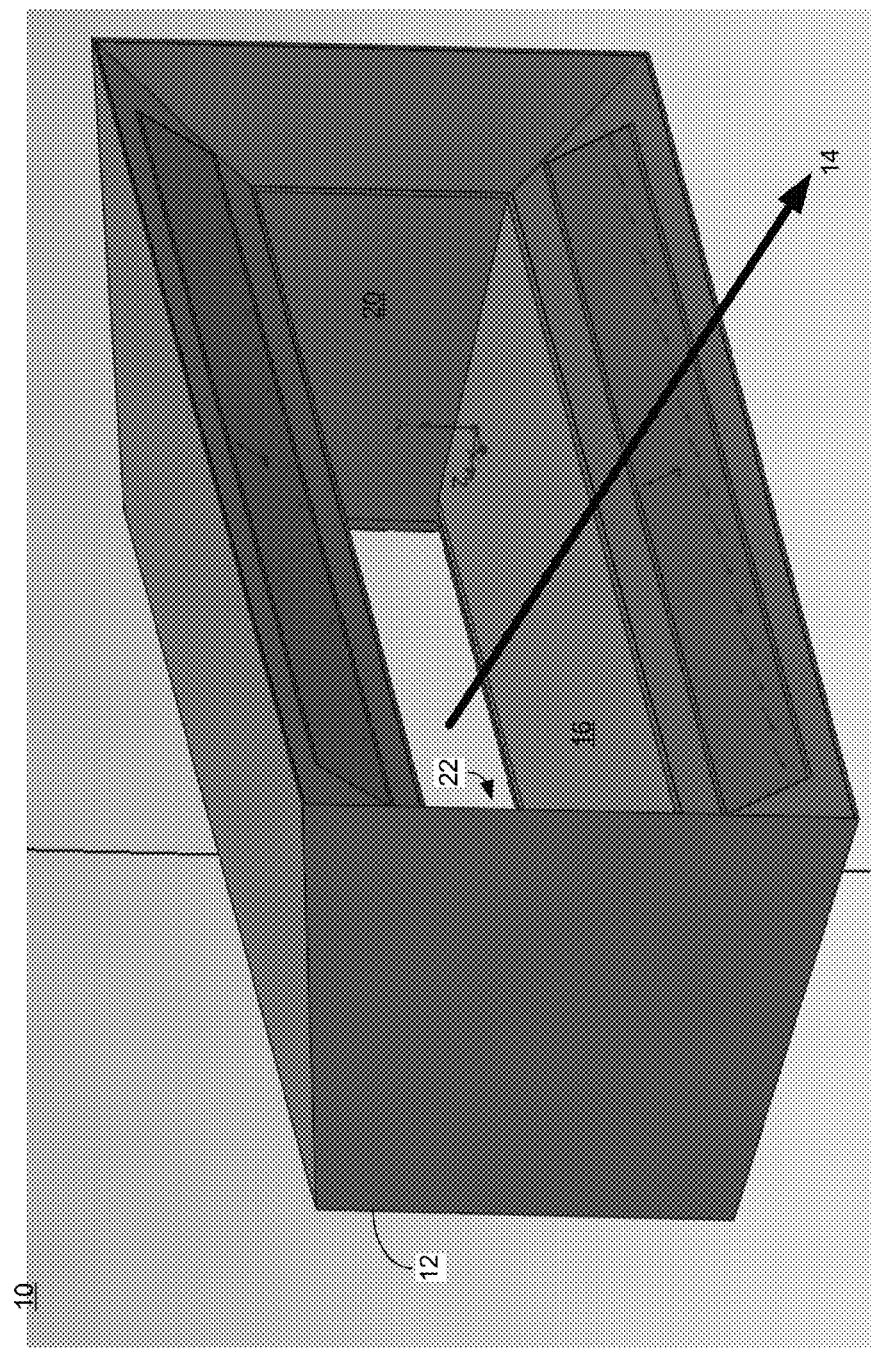
FIG. 1 is a front perspective view of an air treatment apparatus, according to an example embodiment of the present disclosure.
Figure 2:
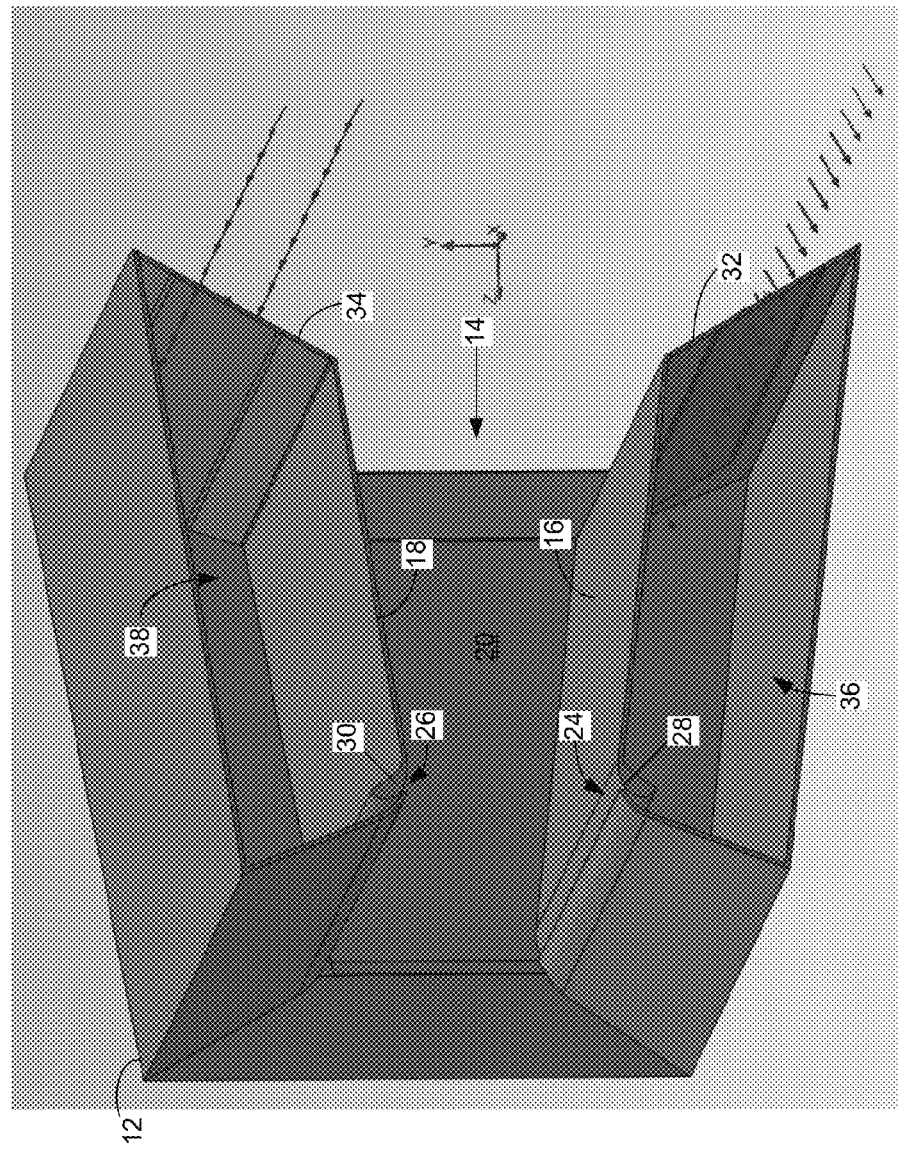
FIG. 2 is a cross-sectional view of a housing of an air treatment apparatus, according to an example embodiment of the present disclosure.
Figure 3:
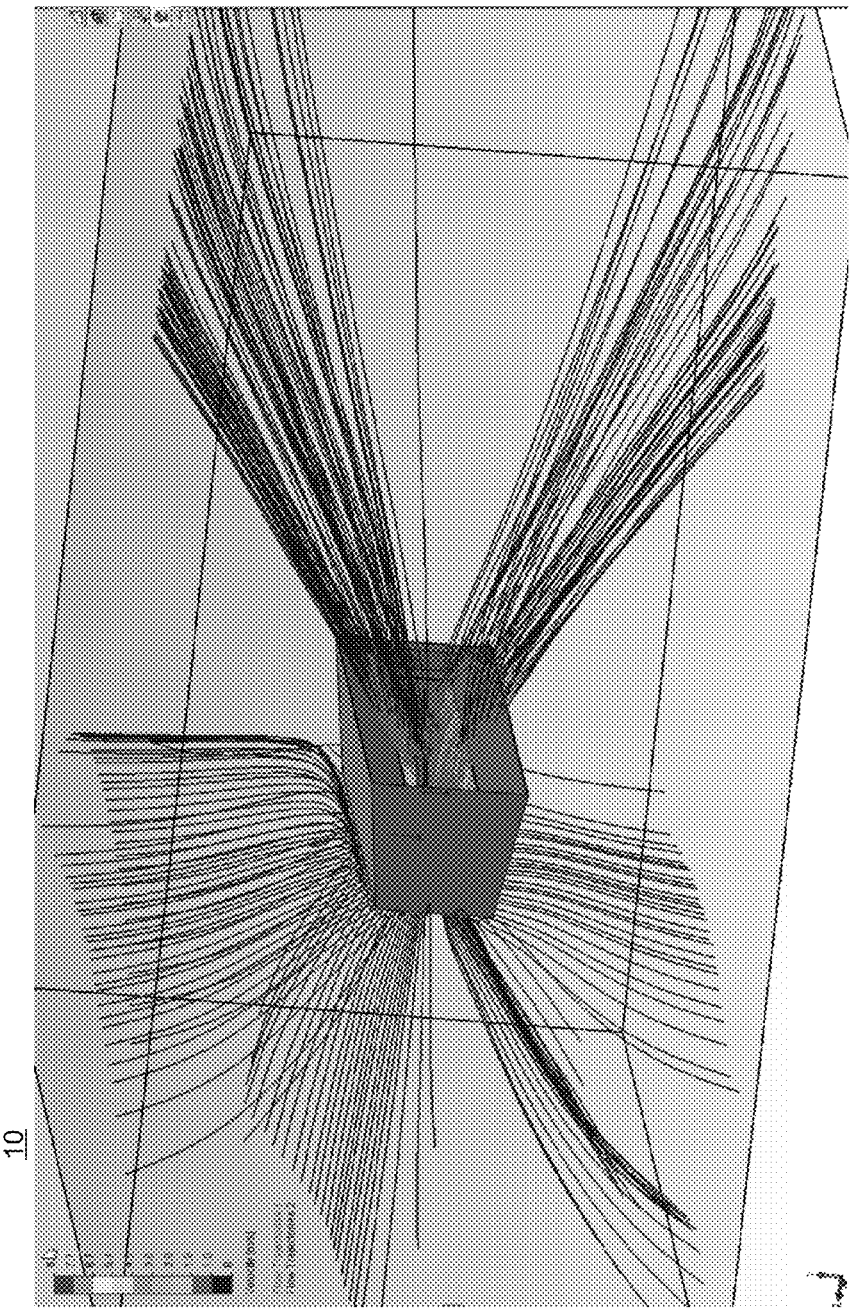
FIG. 3 diagrammatically depicts airflow through a nozzle passage of an air treatment apparatus, according to an example embodiment of the present disclosure.

For example, and referring a to FIGS. 1 and 2, illustrative air treatment apparatus 10 may generally include housing 12, which may generally define nozzle passage 14 extending through at least a portion of housing 12. Nozzle passage 14 may be defined by at least one wall (e.g., wall 16) of housing 12. As shown in FIGS. 1 through 3, in an embodiment, housing 12 may generally define nozzle passage 14 having a generally quadrilateral cross-section (e.g., a rectangular cross-section in the illustrated embodiment). In such an embodiment, housing 12 may generally include four walls (e.g., walls 16, 18, 20, 22) defining generally rectangular cross-section nozzle passage 14. However, it will be appreciated that the nozzle passage may include other cross-sections (e.g., round, oval, and/or other polygonal or semi-polygonal cross-sections). As such, the number of walls defining the nozzle passage may vary. For example, in an embodiment including a round oval cross-section nozzle passage, the nozzle passage may be defined by a single wall.

The at least one wall defining nozzle passage 14 (e.g., one or more of walls 16, 18, 20, 22 in the illustrated embodiment) may include a vent (e.g. vents 24, 26 respectively associated with walls 16, 18, as shown in FIG. 2) adjacent to an upstream portion of the walls 16, 18. As generally described above, a blower (to be described in greater detail below) may create an airflow that may be directed through vents 24, 26 and along at least a portion of walls 16, 18. In an embodiment, nozzle passage 14 may include a Coanda surface (e.g., Coanda surfaces 28, 30) adjacent to respective vents 24, 26. In an embodiment, one or more of Coanda surfaces 28, 30 may form at least a portion of a downstream portion of vents 24, 26. That is, a downstream portion of walls 16, 18 defining vents 24, 26 may include Coanda surfaces 28, 30. In an embodiment, the combination of a Coanda surface adjacent to a vent included in a housing wall defining the nozzle passage may generally be referred to as a Coanda exhaust.

As is generally known, a Coanda surface may generally include a surface having an at least partial airfoil shape which may give rise Coanda effect flow of the air exiting the vent, whereby the air may tend to be attracted to or "stick" to the Coanda surface and/or the walls defining the nozzle passage downstream from the vents. As shown, e.g., in FIG. 2, in an embodiment, Coanda surfaces 28, 30 may allow vents 24, 26 to be generally flush with and/or be generally formed as slits in respective walls 16, 18 of the illustrated embodiment, as the airflow exiting vents 24, 26 may tend to follow Coanda surfaces 28, 30 allowing the airflow to be directed in a downstream direction along walls 16, 18.

In a further embodiment, the vents may have a configuration other than a Coanda exhaust. For example, in an embodiment an upstream (relative to a direction of airflow through the nozzle passage) portion of the wall defining the vent may protrude above the downstream wall portion, such that a vent opening may extend above the downstream wall portion, and may generally direct air exiting the vent along the downstream portion of the wall. Other configurations may similarly be utilized by which the vent may direct air exiting from the vent along the wall. For example, one or more discrete vents or nozzles may be provided which may protrude at least partially into the nozzle passage. Such protruding vents or nozzles may generally direct an airflow exiting the vent or nozzles in a downstream direction through the nozzle passage.

While the depicted embodiment of air treatment apparatus 10 generally depicts vents 24, 26 as being continuous openings generally extending along the upstream width of respective walls 16, 18, it will be appreciated that other configurations may be equally utilized. For example, one or more of the vents may extend less than the entire width of a wall. Similarly, each wall defining the nozzle passage may be provided with one or more discreet vents. Various additional/alternative configurations may be equally utilized.

Consistent with the depicted embodiment, housing 12 of air treatment apparatus 10 may include two opposed walls (e.g., walls 16, 18) defining at least a portion of nozzle passage 14. Further, each of generally opposed walls 16, 18 may include respective vents 24, 26 adjacent an upstream portion of each wall 16, 18 (and thereby, adjacent an upstream portion of nozzle passage 14). Further, in an embodiment, each of vents 24, 26 may be configured as a Coanda exhaust, being provide with respective Coanda surfaces 28, 30 adjacent to a downstream portion of vents 24, 26. In other embodiments, a greater or fewer number of walls defining the nozzle passage may be provided with vents. For example, in an embodiment in which the nozzle passage may have a generally rectangular cross-section, each of the four walls defining the nozzle passage may include vents. In further embodiments, only a single wall defining the nozzle passage may include a vent.

In an embodiment, the combination of the nozzle passage defined by the air treatment apparatus housing and the vents directing an airflow (e.g., which may include an exhaust flow from the blower) in a downstream direction relative to the nozzle passage may create an area of low pressure in a downstream portion of the nozzle passage and/or at a downstream location relative to the housing of the air treatment apparatus. Referring also to FIG. 3, the downstream area of low pressure may cause additional air upstream of the air treatment apparatus to be drown into the nozzle passage, and to be discharged through the downstream end of the nozzle passage. By entraining air via an upstream intake of the nozzle passage, the air treatment apparatus may be capable of creating a greater airflow through the nozzle passage than the airflow that is provided by the blower. That is, the airflow through the air treatment apparatus may be greater than the airflow through the blower. In some embodiments, such a design may create higher exit airflow (cfm) and may thus better distribute the "cleaned" air that is exiting the air treatment apparatus.

In an embodiment, the configuration of the nozzle passage may, at least in part, facilitate the creation of the downstream area of low pressure, and thereby the entrainment of air via an upstream intake of the nozzle passage. For example, in an embodiment, a first portion of the at least one wall defining the nozzle passage may diverge outwardly relative to an axis if the nozzle passage at least at a location that is downstream from the vent. For example, as shown, e.g., in FIG. 2, walls 16, 18 may be angled relative to an axis of nozzle passage 14, such that walls 16, 18 diverge relative to one another and relative to the axis of nozzle passage 14. As will be appreciate, in some embodiments, the divergent arrangement of walls 16, 18 may facilitate the creation of an area of low pressure downstream from vents 24, 26.

Further, in some embodiments, a second portion of the at least one wall may diverge outwardly away from the first portion of the wall relative to the axis of the nozzle passage downstream from the first portion of the wall. For example, as shown, nozzle passage 14 may be further defined, at least in part, by housing wall portions 32, 34. Wall portions 32, 34 may, in some embodiments, include a downstream extension of respective walls 16, 18. As shown, wall portions 32, 34 may be oriented at an outwardly divergent angle relative to walls 16, 18. That is, the angle formed by wall portions 32, 34 relative to the axis of nozzle passage 14 may be greater than the angle formed by walls 16, 18 relative to the axis of nozzle passage 14. The further divergent orientation of wall portions 32, 34 may, in some embodiments, further facilitate the creation of an area of low pressure at a downstream location relative to vents 24, 26, and thereby increase the entrainment of air from outside the upstream intake of nozzle passage 14.

Figure 4:
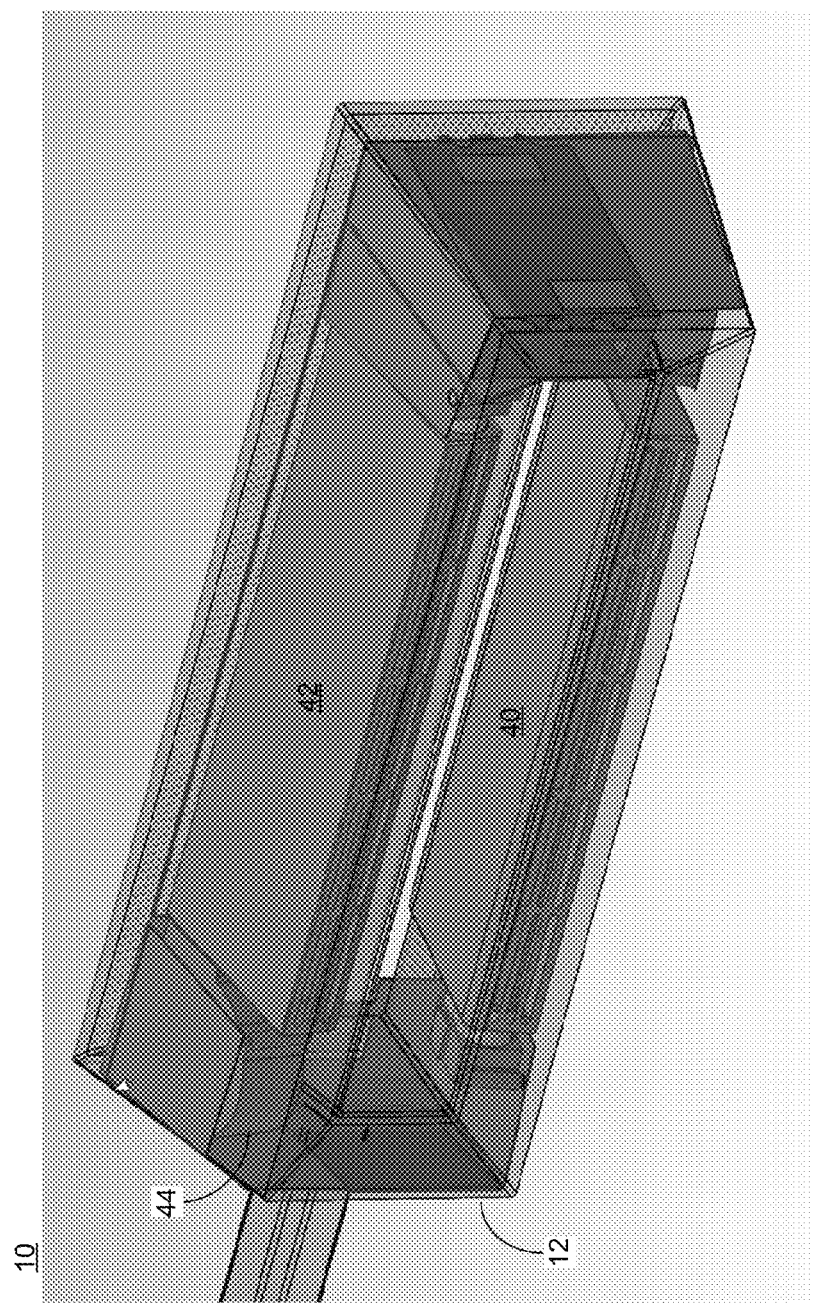
FIG. 4 diagrammatically depicts a partially transparent view of an air treatment apparatus, according to an example embodiment of the present disclosure.
Figure 5:
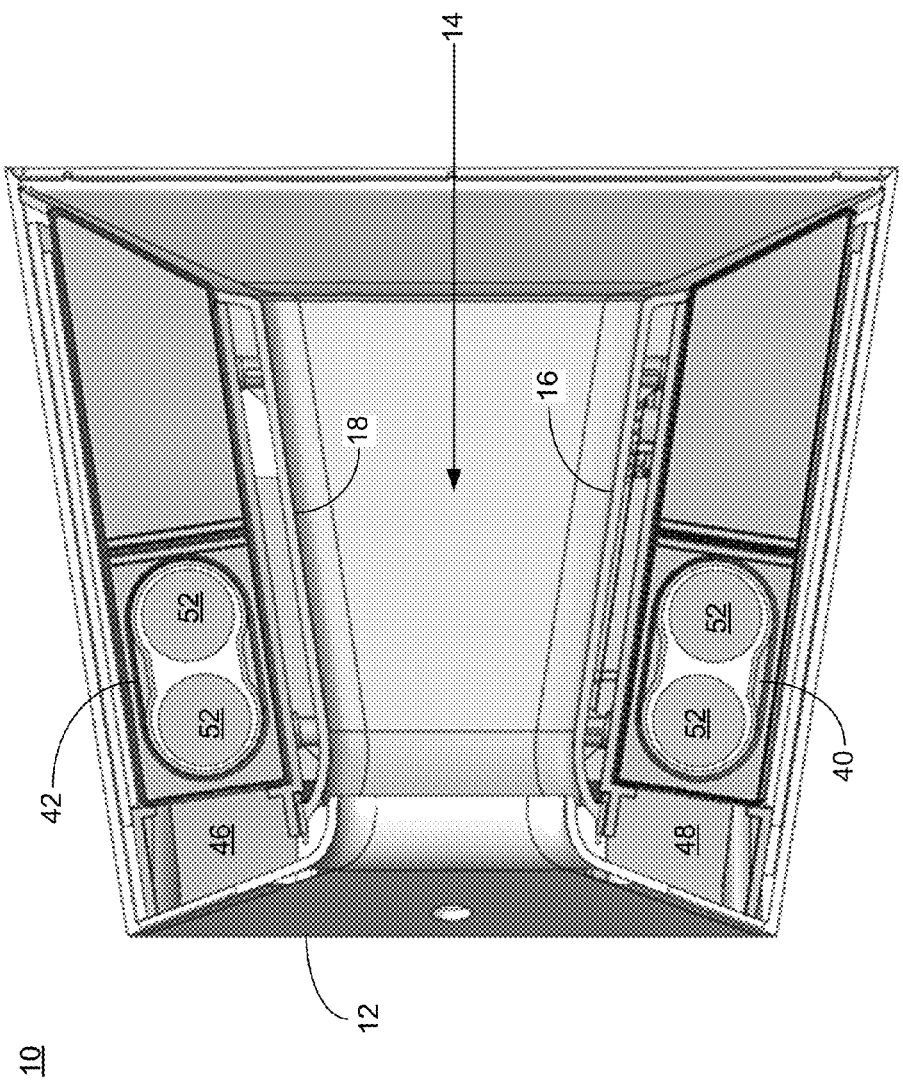
FIG. 5 is a cross-sectional view of an air treatment apparatus, according to an example embodiment of the present disclosure.
Figure 6:
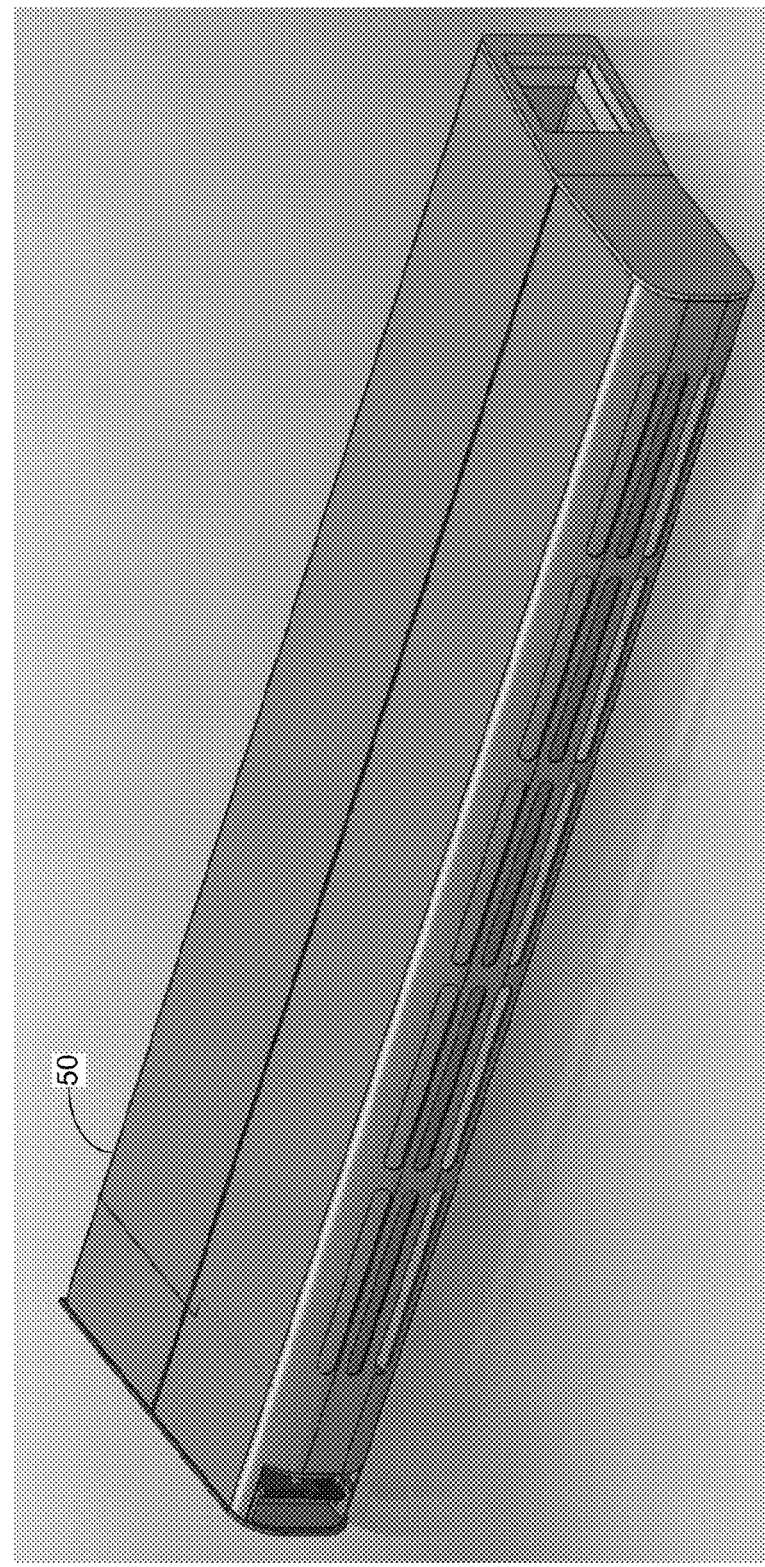
FIG. 6 is a perspective view of a reaction chamber cartridge that may be used in connection with an air treatment apparatus, according to an example embodiment of the present disclosure.
Figure 7:
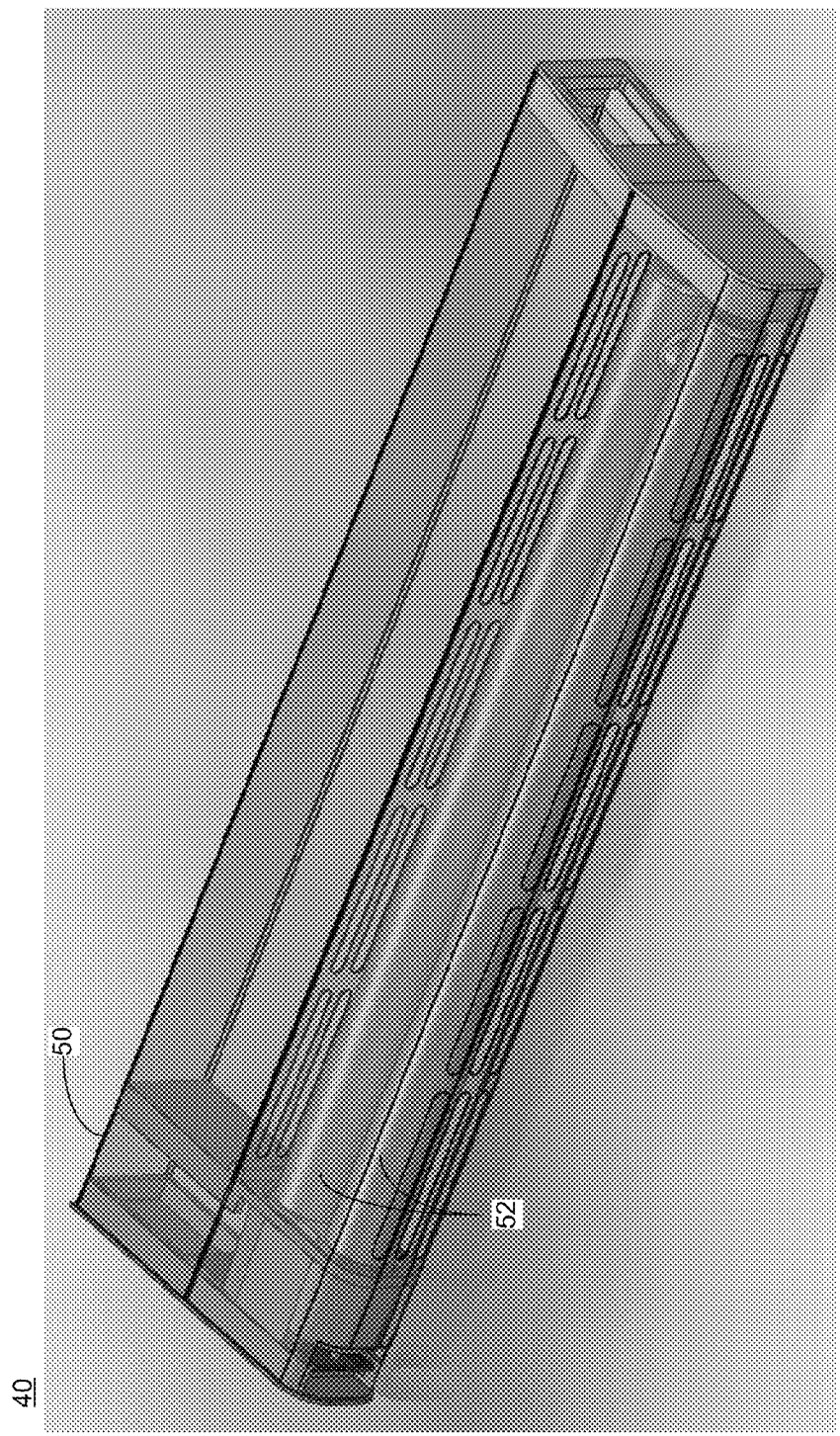
FIG. 7 is a partially transparent perspective view of a reaction chamber cartridge that may be used in connection with an air treatment apparatus, according to an example embodiment of the present disclosure.
Figure 8:
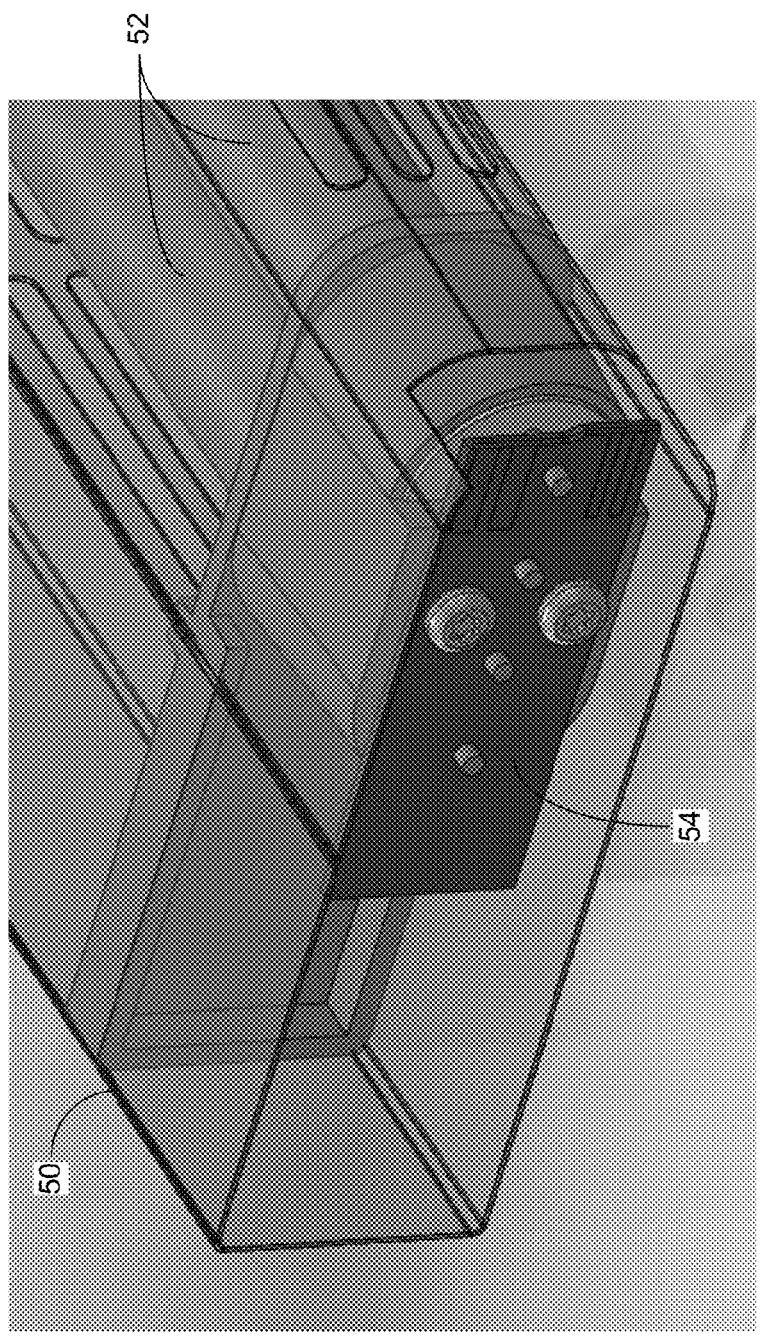
FIG. 8 is a detailed end perspective view of a reaction chamber cartridge that may be used in connection with an air treatment apparatus, according to an example embodiment of the present disclosure.

Referring also to FIGS. 4-5, and as shown in FIG. 2, in an embodiment, housing 12 may define a housing interior (e.g., housing interiors 36, 38), which may at least partially surround nozzle passage 14. As shown, and as will be described in greater detail below, a photocatalytic reaction chamber (e.g., photocatalytic reaction chambers 40, 42, which may be associated with respective vents 24, 26) and a blower (e.g., blower 44) may be at least partially disposed within one or more of housing interiors 36, 38. While the illustrated embodiment depicts two photocatalytic reaction chamber (e.g., photocatalytic reaction chambers 40, 42), various embodiments may utilized one, or more than one photocatalytic reaction chambers. Further, while air treatment apparatus 10 is shown including a single blower (e.g., blower 44), in various embodiments one, or more than one, blowers may be utilized for providing an airflow through the one or more photocatalytic reaction chambers and out through the one or more vents.

In an embodiment, blower 44 may be fluidly coupled to convey air through the photocatalytic reaction chamber and to direct the air through the vent and along at least a portion of the at least one wall. In this regard, in some embodiments, housing 12 may further define a passage (e.g., passages 46, 48) fluidly coupling the blower, the photocatalytic reaction chamber, and the vent. For example, in an embodiment, an airflow generated by blower 44 may cause air to be directed through photocatalytic reaction chambers 40, 42, and to be directed out of vents 24, 26 via passages 46, 48. While only a single blower is depicted in FIG. 4, it will be appreciated that in some embodiments multiple blowers may be utilized (e.g., a separate blower associated with each photocatalytic reaction chamber). Further, in various embodiments, the blower(s) may be fluidly coupled with the photocatalytic reaction chamber to either push air through the photocatalytic reaction chamber, and/or to pull air through the photocatalytic reaction chamber. Blower 44 may include any suitable fan or blower for conveying air, including, but not limited to, an axial fan, a radial blower, a centrifugal air pump, an impeller, etc.

As mentioned above, the air treatment apparatus may include a photocatalytic reaction chamber (e.g., photocatalytic reaction chambers 40, 42 in the illustrative embodiment), which may include a plurality of photocatalytic media and a light source disposed to illuminate at least a portion of the photocatalytic media for producing a photocatalytic reaction generating a plurality of hydroxyl radicals. Photocatalytic reaction chambers 40, 42 may facilitate photocatalytic oxidation air treatment for killing and/or mineralizing bacteria, mold, fungi, spores, mycotoxins, viruses, allergens, other similar organic microorganisms or agents, and for oxidizing volatile organic compounds (VOC's).

Consistent with the present disclosure, the photocatalytic reaction chambers may include the photocatalytic media an a light source. When illuminated by the light source, at least a portion of the photocatalytic media may product a photocatalytic reaction that may generally a plurality of hydroxyl radicals. The hydroxyl radicals (OH—) produced by the photocatalytic reaction may be generally substantially surface bound (i.e. may exist along the surfaces of the photocatalytic media) and thus may generally not exit the photocatalytic reaction chamber. In some embodiments, the hydroxyl radicals produced by the photocatalytic reaction may be nearly 100% surface bound on the photocatalytic media. As the hydroxyl radicals may be substantially surface bound on the photocatalytic media, the photocatalytic oxidation may be substantially safe, e.g., for use around and/or in connection with perishable products, fixtures, as well as humans. This may be contrasted, for example, with systems using ozone, which may create a "free" floating hydroxyl radical (OH—) that may attack anything organic in the room being treated (e.g., also including human immune systems). Further, in some embodiments, the photocatalytic oxidation provided by an air treatment system herein may be capable of killing, mineralizing, and/or oxidizing small particles such as viruses and VOC's, which may be of a size that even HEPA filters may not be capable of removing.

Additionally, in some embodiments, the photocatalytic reaction chamber of the present disclosure may be self cleaning. For example, in some embodiments, the reaction by products of killing and/or mineralizing bacteria, mold, fungi, spores, mycotoxins, viruses, allergens, other similar organic microorganisms or agents, and of oxidizing volatile organic compounds (VOC's) may generally include carbon dioxide and/or water vapor. Such reaction byproducts may be released through the media. As such, the reaction byproducts may generally not build up on the photocatalytic media. Accordingly, in some embodiments, need or frequency of replacing the photocatalytic media may be reduced and/or eliminated.

In some embodiments, the photocatalytic media may include a media substrate coated with a micro-porous nano-particle membrane including a photocatalytic substance. This media substrate is non-reactive with the photocatalytic substance and thus induces the photocatalytic substance to form on each media substrate as a nano-particle structure rather than as a merely closed packed layer According to various examples, the media substrate may include, glass-type materials, bora silica glass, ceramic materials, metallic materials, plastics, etc. In this regard, materials that may normally be reactive with a photocatalytic substance applied thereto, may be pre-coated with another substance that renders them non-reactive with the photocatalytic substance prior to coating them with the photocatalytic substance. Further, the media substrate may be provided having various shapes and configurations, e.g., which may provide relatively high surface area while permitting adequate airflow through the photocatalytic reaction chamber. For example, the media substrate may be provided having cylindrical, spherical, tubular, toroidal, polyhedrical, or other suitable shapes.

According to an embodiment, the photocatalytic substance may include TiO2 and the light source may emit ultraviolet light having a wavelength less than about 400 nm. In further embodiments, the photocatalytic substance may include at least one of ZnO and a WO3, and the light source may emit light in the visible spectrum. Any suitable light sources emitting light in the activating wavelengths may be utilized in connection with the present disclosure, including, but not limited to, fluorescent light sources, incandescent light sources, LED light sources, etc. Various additional/alternative photocatalytic substances may be utilized, which may, when illuminated with light of an appropriate wavelength, generate hydroxyl radicals that may be capable of killing and/or mineralizing bacteria, mold, fungi, spores, mycotoxins, viruses, allergens, other similar organic microorganisms or agents, and for oxidizing volatile organic compounds (VOC's).

In some embodiments, the photocatalytic media may include a single photocatalytic substance (e.g., TiO2, ZnO, WO3), and/or may include combinations of photocatalytic substances. Further, in some embodiments, the photocatalytic media may include one or more enhancing substances. An enhancing substance may, for example, increase the reaction rate of the photocatalytic reaction, which may increase the number of hydroxyl radicals that may be generated and/or available for an oxidation reaction.

As generally described above, in some embodiments the media substrate may be coated with a micro-porous nano-particle membrane including the photocatalytic substance. The photocatalytic substance may be coated on the media substrate to provide a micro-porous nano-particle membrane according to any suitable techniques, example of which techniques may be disclosed in U.S. Pat. No. 5,006,248, issued 9 Apr. 1991, to Anderson, et al.; U.S. Pat. No. 5,035,784, issued 30 Jul. 1991, to Anderson, et al.; and U.S. Pat. No. 5,227,342, issued 13 Jul. 1993, to Anderson, et al., the entire disclosure of all of which are incorporated herein by reference.

In an embodiment, providing the photocatalytic substance as a micro-porous nano-particle membrane on the media substrate may dramatically increases the number of reaction sites available for bacteria, mold, fungi, spores, mycotoxins, viruses, allergens, other similar organic microorganisms and/or agents, and VOC's to be killed, mineralized, and/or oxidized by the hydroxyl radicals (OH—) produced as part of the photocatalytic reaction, when the media substrate coated with the photocatalytic substance is exposed to an activating light (for example, ultraviolet light, e.g., generally having a wavelength less than about 400 nm, in the case of a media coated with $TiO_2$, or visible light in the case of a media coated with ZnO and/or $WO_3$). By dramatically increasing the number of available reaction sites and increasing the number of such oxidation reactions that occur, efficacy for treating air by killing, mineralizing, and/or oxidizing bacteria, mold, fungi, spores, mycotoxins, viruses, allergens, other similar organic microorganisms and/or agents, and VOC's may be greatly improved.

In addition/as an alternative to increasing the number of reaction sites, providing the photocatalytic substance as a micro-porous nano-particle membrane on the media substrates may, in some embodiments, create a relatively durable and/or permanent bond between the photocatalytic substance and the media substrate. The bond between the photocatalytic substance and the media substrate may be achieved, at least in part, as a result of a dopant used in connection with the production of the photocatalytic substance (e.g., which may, in some embodiments, include a techniques described in one or more of the above-referenced US Patents), which may prevent and/or reduce the photocatalytic substance (e.g., $TiO_2$, $ZnO$, $WO_3$, etc.) from migrating and clumping up (e.g. during the coating process). The photocatalytic substance may typically not delaminate from the media substrates. This may, in some instances, provide a significant advantage over other $TiO_2$ coated filters and/or devices using photocatalytic oxidation technology, e.g., which may experience delamination and may need to be replaced.

Figure 9:
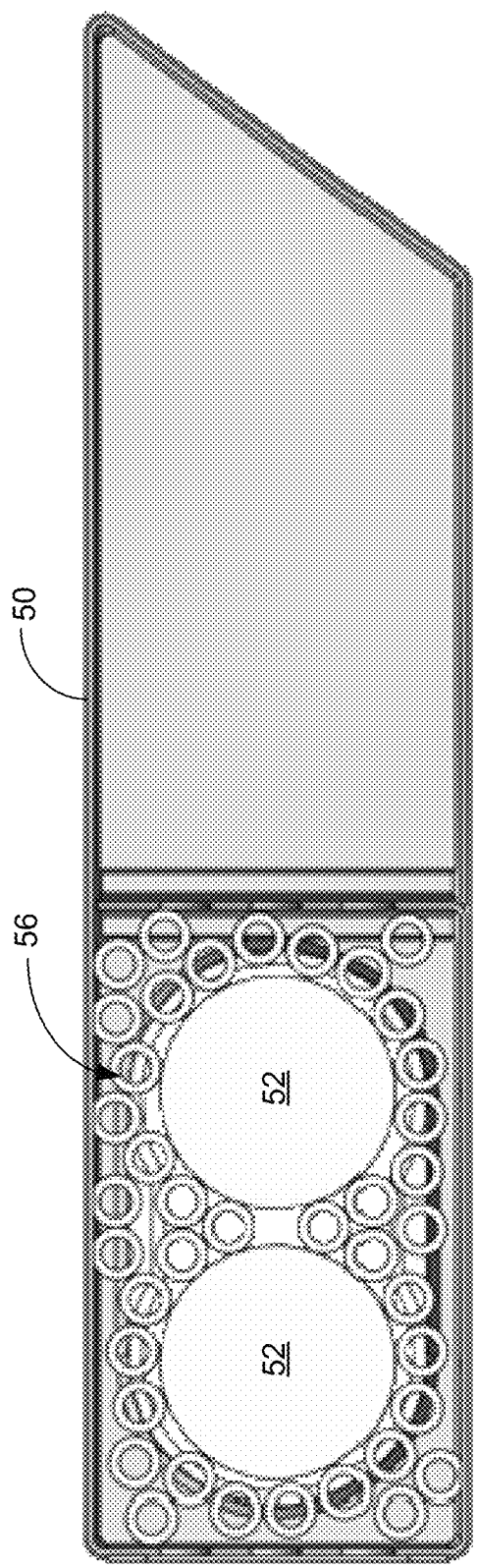
FIG. 9 is a cross-sectional view of a reaction chamber cartridge that may be used in connection with an air treatment apparatus, according to an example embodiment of the present disclosure.

In an embodiment, and referring also to FIGS. 6 through 10, the photocatalytic reaction chamber may include a removable reaction chamber cartridge. For example, at least a portion of the plurality of photocatalytic media and the light source may be at least partially contained within the reaction chamber cartridge. For example, photocatalytic reaction chamber 40 may include removable reaction chamber cartridge 50. Light source 52 may be at least partially disposed within removable reaction chamber cartridge 50. While light source 52 is illustrated as a fluorescent-tube type light source, such depiction is intended only for the purpose of illustration as other suitable light source configurations may suitably utilized. Removable reaction chamber cartridge 50 may additionally provide one or more connection features 54, e.g., which may provide electrical and/or mechanical connection between removable reaction chamber cartridge (e.g., including light source 52) and one or more power supplies and/or control circuits associated with air treatment apparatus 10. As shown in FIG. 9, at least a portion of light source 52 may be at least partially surrounded by at least a portion of the plurality of photocatalytic media 56.

In an embodiment, removable reaction chamber cartridge 50 may be configured to be releasable coupled with housing 12. For example, at least apportion of removable reaction chamber cartridge 50 may be received within housing interiors 36, 38 of housing 12. Further, removable reaction chamber cartridge 50 may be releasably coupled with housing 12, e.g., via one or more spring latches 58, or other suitable retentions features (e.g., snap-fits, screws, clips, etc.). In an embodiment, the releasable coupling of removable reaction chamber cartridge 50 with housing 12 may facilitate user removal and/or replacement of removable reaction chamber cartridge 50. For example, in an embodiment, it may be desirable to periodically (e.g., once a year, once every several years, or at other suitable intervals) replace one or more of the light source and the photocatalytic media to maintain useful air treatment performance of the photocatalytic reaction. Removable reaction chamber cartridge 50 may allow facile replacement of both the photocatalytic media and the light source, which may both be contained within removable reaction chamber cartridge 50.

Figure 11:
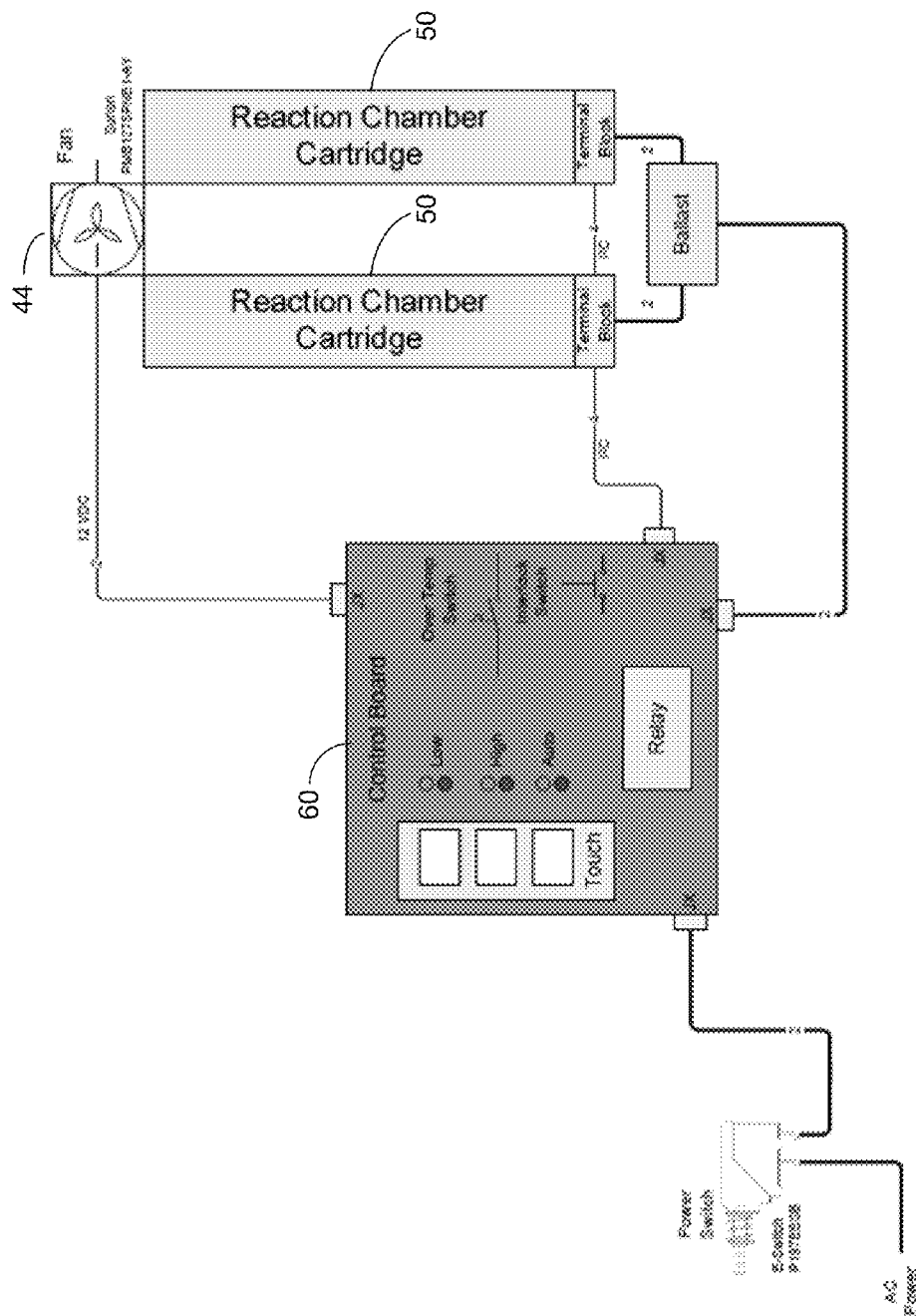
FIG. 11 schematically depicts an air treatment apparatus, according to an example embodiment of the present disclosure.

With reference also to FIG. 11, air treatment apparatus 10 may include one or more control systems (e.g., control system 60). Control system 60 may be coupled for controlling the operation of one or more of blower 44 and removable reaction chamber cartridge 50 (e.g., light source 52 included within removable reaction chamber cartridge 50), and/or provide other control functionality. For example, as discussed above, in some embodiments, it may be desirable to replace removable reaction chamber cartridge at periodic intervals. In an embodiment, the replacement cycle (e.g., the time between cartridge replacement) may vary depending on various factors, such as light source type, frequency of use, as well as other factors. For example, in various example embodiments, removable reaction chamber cartridge 50 may have a one year replacement cycle, a two year replacement cycle, a five year replacement cycle, or other suitable replacement cycle. In an example embodiment, in which the replacement cycle may be a 12 month cycle, control system 60 may monitor a usage sensor/timer (e.g., which may include a sensor associated with removable reaction chamber cartridge 50 and/or a usage timer that may be associated with control system 60 and/or removable reaction chamber cartridge 50). Upon the detection of 11 months of operation (and/or another suitable interval), control system 60 may activate an indicator light alerting the user that it is time to order a replacement removable reaction chamber cartridge (i.e. which may include the light source and the photocatalytic media). Upon replacement of removable reaction chamber cartridge, the usage timer may begin to measure usage of the new removable reaction chamber cartridge, and may accumulate time when the air treatment apparatus is operating.

In some embodiments, blower 44 may be capable of operating at multiple speeds (e.g., a high speed and a low speed), which may provide relative airflow. In an embodiment, the speed of blower 44 may be controlled via control system 60. For example, control system 60 may allow a user of air treatment apparatus 10 to manually select between the different blower speeds. Further, in an embodiment, control system 60 may provide an automatic blower speed control. In response to receiving an input (e.g., via a suitable user interface) for automatic blower speed control, control system 60 may operate blower 44 at a first blower speed (for example, at a high blower speed) until a desired pre-set condition in the room (for example, an ambient light level, a temperature in the room, etc.). In response to detecting the pre-set condition, control system 60 may automatically switch to operating blower 44 at a second blower speed (e.g., a low blower speed). In an embodiment in which the pre-set condition may be a level of darkness (e.g., light level) measured by control system 60, the automatic blower speed control provided by control system 60 may allow air treatment apparatus 10 to operate at a relatively quiet noise level (e.g., as may be provided by a lower blower speed) at night time.

In a similar manner to the automatic control of the blower speed based on a pre-set condition, control system 60 may similarly control an illumination level of any indicator lights/LED's and/or user interface illumination levels. For example, upon detecting an ambient light level below a pre-set threshold control system 60 may reduce the illumination level of any indicator lights/LED's and/or user interface illumination levels to a predetermined "night time" illumination level. The reduction in the illumination level may, for example, thereby reduce the light pollution generated at night. Correspondingly, in response to detecting an ambient light level above a pre-set threshold, control system 60 may increase the illumination level of any indicator lights/LED's and/or user interface illumination levels to a predetermined "day time" illumination level.

In an embodiment, control system 60 may further provide one or more safety features. For example, control system 60 may be configured to provide an over-temperature shut-off. For example, air treatment apparatus 10 may include an over-heat sensor (e.g., a thermal switch, which may be associated with one or more of blower 44, light source 52/removable reaction chamber cartridge 50, and/or control system 60). A temperature above a preset threshold temperature may be indicative of, for example, a malfunction or failure of blower 44 and/or light source 52. In response to detecting (via the over-heat sensor) a temperature above a preset threshold temperature (e.g. an over-temperature condition), the over-heat sensor and/or control system 60 may power-down air treatment apparatus 10 (e.g., and/or blower 44 and light source 52). In an embodiment, in addition to powering-down air treatment apparatus 10, control system 60 may active a warning indicator light in response to detecting the over-temperature condition. In some embodiments, air treatment apparatus 10 may remain powered-down until the detected temperature falls below a preset safe operation temperature, and/or until manually reset by a user.

Figure 10:
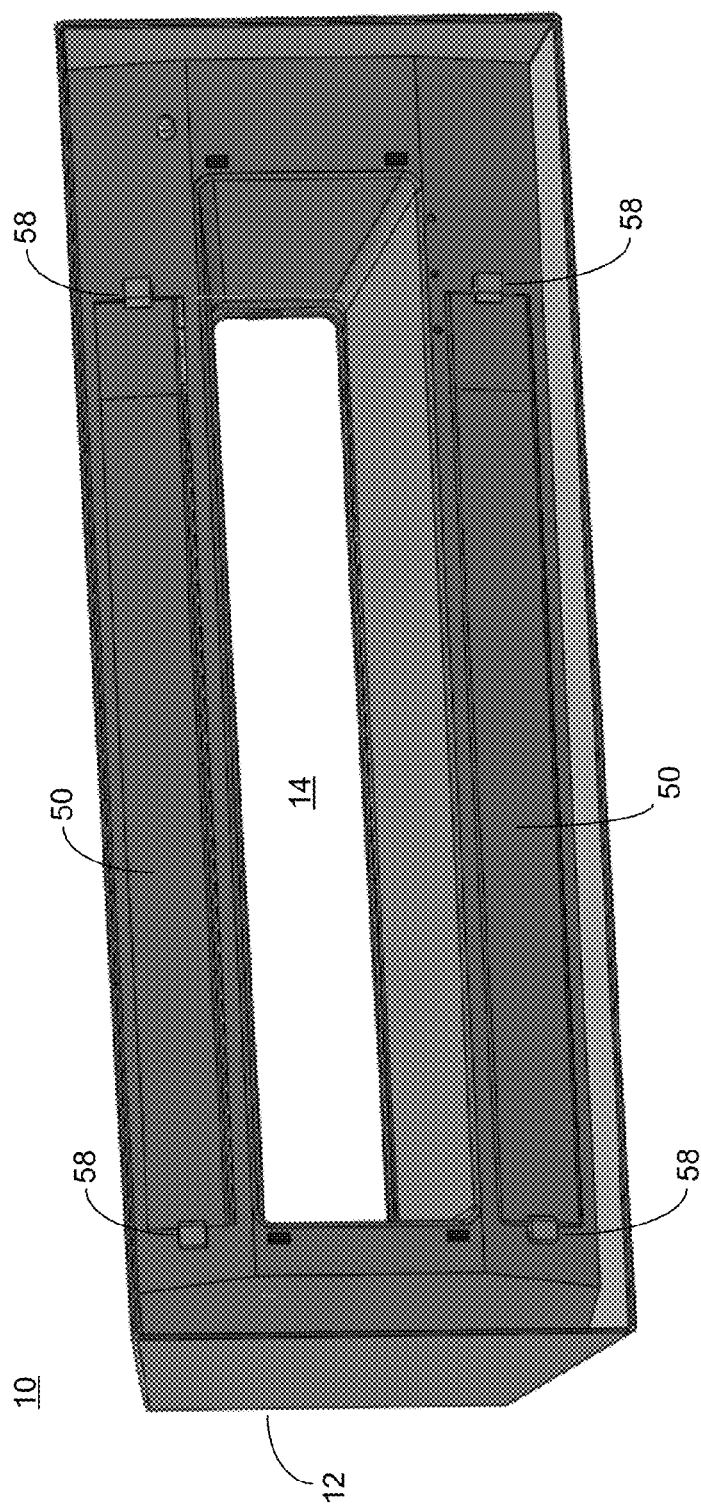
FIG. 10 is a perspective view of an air treatment apparatus including two reaction chamber cartridges coupled with a housing, according to an example embodiment of the present disclosure.

With continued reference to FIG. 10, and referring also to FIG. 12, in an embodiment, air treatment apparatus 10 may provide facile access to removable reaction chamber cartridge 50. For example, grill 62 may removably attach to housing 12, e.g., via snap-fits, spring clips, or other suitable removable attachment mechanism. Removable reaction chamber cartridge(s) 50 and latches may be accessible with grill 62 removed from housing 12. As such, with grill 62 detached from housing 12, removable reaction chamber cartridge 50 may be removed/replaced, and grill 62 may subsequently be reattached to housing 12. Further, in an embodiment, grill 62 may also protect, decoratively cover, and/or provide filtering of air intake (as indicated by arrows in FIG. 2) into housing interior 36, 38, which may be fluidly coupled with an air intake of blower 44 and/or photocatalytic reaction chambers 40, 42/removable reaction chamber cartridge 50.

In some embodiments, air treatment apparatus 10 may be provided having a relatively compact design. The relatively compact design may, for example, allow for easy installation of air treatment apparatus 10. Further, the relatively compact design may also make air treatment apparatus 10 relatively easy to move from one location to another. Air treatment apparatus may, suitably be used in a variety of locations including, but not limited to, bedrooms, bathrooms, kitchens, living rooms, studies, dining rooms, family rooms, etc. For example, air treatment apparatus 10 may suitably be located on top of a desk, dresser, cabinet, table, storage bin, etc. Further, air treatment apparatus 10 may be used in conjunction with a stand, or it can be mounted to a wall and/or ceiling.

Figure 14:
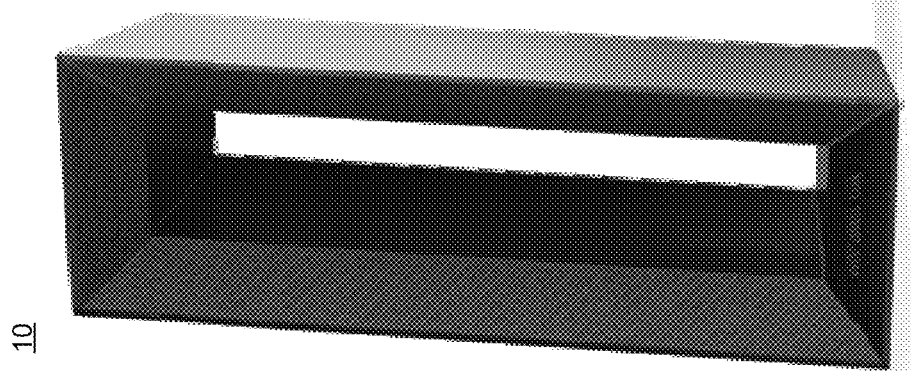
FIG. 14 depicts a vertical implementation of an air treatment apparatus, according to an example embodiment of the present disclosure.
Figure 13:
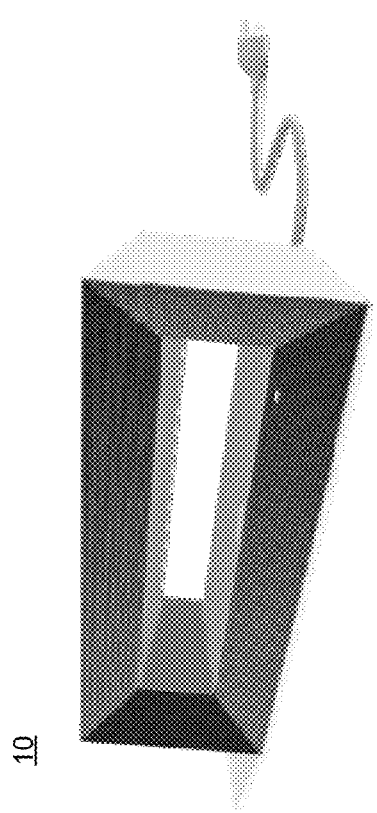
FIG. 13 depicts a horizontal implementation of an air treatment apparatus, according to an example embodiment of the present disclosure.

In this regard, and referring also to FIGS. 13-14, air treatment apparatus may suitably be placed and/or mounted in a horizontal configuration (as shown in FIG. 13) and/or a vertical configuration (as shown in FIG. 14).

A number of implementations have been described. Nevertheless, it will be understood that various modifications may be made. Accordingly, other implementations are within the scope of the following claims.

What is claimed is:

1. An apparatus comprising:
    a housing including at least one wall defining a nozzle passage extending through at least a portion of the housing, the nozzle passage having a vent adjacent an upstream portion of the at least one wall, the housing including one or more housing interiors at least partially surrounding the nozzle passage;
    a photocatalytic reaction chamber at least partially disposed within at least one of the one or more housing interiors at least partially surrounding the nozzle passage, the photocatalytic chamber including a plurality of photocatalytic media and a light source disposed to illuminate at least a portion of the photocatalytic media for producing a photocatalytic reaction generating a plurality of hydroxyl radicals; and
    a blower at least partially disposed within at least one of the one or more housing interiors at least partially surrounding the nozzle passage, the blower fluidly coupled with the photocatalytic reaction chamber for conveying air through the photocatalytic reaction chamber and directing the air through the vent and along at least a portion of the at least one wall.

2. The apparatus of claim 1, wherein the nozzle passage includes a Coanda surface adjacent to the vent.

3. The apparatus of claim 1, wherein a first portion of the at least one wall diverges outwardly relative to an axis of the nozzle passage downstream from the vent.

4. The apparatus of claim 3, wherein a second portion of the at least one wall diverges outwardly away from the first portion of the wall relative to the axis of the nozzle passage downstream from the first portion of the wall.

5. The apparatus of claim 1, wherein the housing includes at least two generally opposed walls defining the nozzle passage, each wall including a vent adjacent and upstream portion of each wall.

6. The apparatus of claim 5, wherein the nozzle passage has a generally quadrilateral cross-section.

7. The apparatus of claim 1, wherein the housing further defines a passage fluidly coupling the blower, the photocatalytic reaction chamber, and the vent.

8. The apparatus of claim 1, wherein the photocatalytic reaction chamber includes a removable reaction chamber cartridge, the plurality of photocatalytic media and the light source at least partially contained within the reaction chamber cartridge, the reaction chamber cartridge configured to be at least partially received within at least one of the one or more housing interiors and configured to be releasably coupled with the housing.

9. The apparatus of claim 1, wherein the photocatalytic media includes a media substrate coated with a micro-porous nano-particle membrane including a photocatalytic substance.

10. The apparatus of claim 9, wherein the photocatalytic substance includes $TiO_2$ and the light emits ultraviolet light having a wavelength less than about 400 nm.

11. The apparatus of claim 9, wherein the photocatalytic substance includes at least one of $ZnO$ and a $WO_3$, and the light source emits light in the visible spectrum.

12. The apparatus of claim 1, wherein the blower is configured to push the air through the photocatalytic reaction chamber.

13. The apparatus of claim 1, wherein the blower is configured to pull the air through the photocatalytic reaction chamber.

14. An apparatus comprising:
    a housing defining a nozzle passage extending through at least a portion of the housing, the housing having at least one Coanda exhaust adjacent to an upstream portion of the nozzle passage;
    a photocatalytic reaction chamber cartridge at least partially disposed within an interior defined by the housing and at least partially surrounding the nozzle passage, the photocatalytic reaction chamber cartridge removably coupled with the housing, the photocatalytic reaction chamber cartridge including a photocatalytic reaction chamber including a plurality of photocatalytic media and a light source disposed to illuminate at least a portion of photocatalytic media for producing a plurality of hydroxyl radicals from a photocatalytic reaction of the photocatalytic media;

a blower at least partially disposed within the interior defined by the housing and fluidly coupled with the photocatalytic reaction chamber cartridge and the at least one Coanda exhaust for conveying air through the photocatalytic reaction chamber and out through the at least one Coanda exhaust.

15. The apparatus of claim 14, wherein the photocatalytic media include a substrate coated with a micro-porous nano-particle membrane of a photocatalytic substance.

16. The apparatus of claim 15, wherein the photocatalytic media includes a $TiO_2$ photocatalytic substance, and the light source includes a UV light source emitting light having a wavelength less than about 400 nm.

17. The apparatus of claim 15, wherein the photocatalytic media include one of a ZnO and a $WO_3$ photocatalytic substance, and the light source emits light in the visible spectrum.

18. The apparatus of claim 14, wherein the housing includes four walls defining the nozzle passage having a generally rectangular cross-section.

19. The apparatus of claim 18, including at least two generally opposed Coanda exhausts associated with two generally opposed walls defining the nozzle passage.

20. The apparatus of claim 19, including two photocatalytic reaction chamber cartridges, one photocatalytic reaction chamber cartridge associated with each of the two generally opposed Coanda exhausts.

21. An apparatus comprising:

a housing including four walls defining a nozzle passage extending through at least a portion of the housing and having a generally rectangular cross-section, two opposed walls including a respective Coanda exhaust adjacent to an upstream portion of the nozzle passage;

a photocatalytic reaction chamber cartridge at least partially disposed within an interior defined by the housing an at least partially surrounding the nozzle passage and removably coupled with the housing, the photocatalytic reaction chamber cartridge including a photocatalytic reaction chamber including a plurality of photocatalytic media and a light source disposed to illuminate at least a portion of photocatalytic media for producing a plurality of hydroxyl radicals from a photocatalytic reaction of the photocatalytic media;

a blower at least partially disposed within the interior defined by the housing and fluidly coupled with the photocatalytic reaction chamber cartridge and the at least one Coanda exhaust for conveying air through the photocatalytic reaction chamber and out through the at least one Coanda exhaust.

* * * * *